United States Patent
Kårekull (10) Patent No.: US 12,115,039 B2
(45) Date of Patent: Oct. 15, 2024

(54) HEARING PROTECTION DEVICE

(71) Applicant: 3M INNOVATIVE PROPERTIES COMPANY, St. Paul, MN (US)

(72) Inventor: Oscar Kårekull, Huskvarna (SE)

(73) Assignee: 3M Innovative Properties Company, St. Paul, MN (US)

( * ) Notice: Subject to any disclaimer, the term of this patent is extended or adjusted under 35 U.S.C. 154(b) by 41 days.

(21) Appl. No.: 18/001,126

(22) PCT Filed: Jun. 4, 2021

(86) PCT No.: PCT/IB2021/054904
§ 371 (c)(1),
(2) Date: Dec. 8, 2022

(87) PCT Pub. No.: WO2021/250518
PCT Pub. Date: Dec. 16, 2021

(65) Prior Publication Data
US 2023/0225905 A1    Jul. 20, 2023

Related U.S. Application Data

(60) Provisional application No. 62/705,057, filed on Jun. 9, 2020.

(51) Int. Cl.
*A61F 11/14* (2006.01)
*A61F 11/12* (2006.01)
*H04R 1/20* (2006.01)

(52) U.S. Cl.
CPC .............. *A61F 11/14* (2013.01); *A61F 11/12* (2013.01)

(58) Field of Classification Search
CPC ... H04R 1/08; H04R 1/10; H04R 1/32; H04R 1/086; H04R 1/1008; H04R 1/326;
(Continued)

(56) References Cited

U.S. PATENT DOCUMENTS 12,951 A * 5/1855 Hyde .................. A61F 11/30
181/136
2,643,729 A * 6/1953 McCracken .......... H04R 5/027
181/158
(Continued)

FOREIGN PATENT DOCUMENTS

EP    2782533 B1    9/2015
EP    2866464 B1    8/2018
(Continued)

OTHER PUBLICATIONS

Casali, "Effects of user training with electronically-modulated sound transmission hearing protectors and the open ear on horizontal localization ability", International Journal of Audiology, 2015, vol. 54, No. 01, pp. 1-6.
(Continued)

*Primary Examiner* — Edgardo San Martin
(74) *Attorney, Agent, or Firm* — Katherine M. Scholz (57) ABSTRACT

A hearing protection device is presented. The hearing protection device includes a first and second earmuffs (202, 260, 310) connected by a connector (270, 320). The first and second earmuffs are configured to provide level dependent hearing protection. The first earmuff includes a microphone element (204, 330) having a microphone entry (264), positioned on an exterior of a housing of the first earmuff (260), the microphone element (204, 330) being configured to receive an ambient sound. The first earmuff also includes a processor configured to process the ambient sound using a level dependent function. The first earmuff also includes a speaker configured to broadcast the processed ambient sound in an interior of the first earmuff. The first earmuff also includes an asymmetrical windscreen (262) configured to enclose the microphone element. The windscreen is coupled to the housing of the first earmuff.

17 Claims, 9 Drawing Sheets

(58) Field of Classification Search
CPC .... H04R 1/1083; H04R 1/1016; H04R 5/033; H04R 25/50; H04R 25/552; H04R 2410/07; H04R 2460/01; A61F 11/14; A61F 11/145; A61F 11/08; A61F 11/06
See application file for complete search history.

(56) References Cited

U.S. PATENT DOCUMENTS

| | | | | |
|---|---|---|---|---|
| 3,513,937 | A * | 5/1970 | Moshier | G09B 23/30 181/129 |
| 4,570,746 | A * | 2/1986 | Das | H04R 1/086 381/359 |
| 4,677,678 | A * | 6/1987 | McCutchen | H03G 3/3015 381/72 |
| 6,108,431 | A * | 8/2000 | Bachler | H04R 25/70 381/318 |
| 6,801,629 | B2 * | 10/2004 | Brimhall | A61F 11/08 381/94.1 |
| 7,430,300 | B2 * | 9/2008 | Vosburgh | H04R 3/005 181/129 |
| 8,243,943 | B2 * | 8/2012 | Nordin | H04R 1/1083 381/72 |
| 8,649,525 | B2 * | 2/2014 | Birgersson | A61F 11/14 381/72 |
| 9,084,053 | B2 * | 7/2015 | Parkins | H04R 1/086 |
| 9,232,292 | B2 * | 1/2016 | Haapapuro | H04R 1/086 |
| 10,299,047 | B2 * | 5/2019 | Meyer | H04R 25/70 |
| 2005/0169489 | A1 | 8/2005 | Cleckler et al. | |
| 2006/0140416 | A1 * | 6/2006 | Berg | A61F 11/12 381/72 |
| 2011/0274284 | A1 * | 11/2011 | Mulder | G10K 11/17873 381/72 |
| 2014/0198932 | A1 | 7/2014 | Parkins | |
| 2014/0254852 | A1 | 9/2014 | Haapapuro et al. | |
| 2015/0249892 | A1 * | 9/2015 | Kuhnel | H04R 25/407 381/315 |
| 2017/0374455 | A1 | 12/2017 | Shastry et al. | |
| 2018/0176696 | A1 * | 6/2018 | Voigt Pedersen | H04R 25/505 |
| 2019/0318719 | A1 * | 10/2019 | Copt | A61F 11/14 |
| 2020/0178638 | A1 | 6/2020 | Morales Velasquez | A42B 3/16 |
| 2022/0362059 | A1 * | 11/2022 | Henry | H04R 1/1083 |
| 2023/0114196 | A1 * | 4/2023 | Reibner | A61F 11/12 455/518 |

FOREIGN PATENT DOCUMENTS

| | | | | |
|---|---|---|---|---|
| EP | 3826321 | A1 * | 5/2021 | A61F 11/14 |
| EP | 3456299 | B1 | 11/2021 | |
| GB | 2500251 | A * | 9/2013 | G10K 11/175 |
| WO | 2021064658 | A1 | 4/2021 | |
| WO | 2021105818 | A1 | 6/2021 | |
| WO | 2021116886 | A1 | 6/2021 | |

OTHER PUBLICATIONS

International Search Report for PCT International Application No. PCT/IB2021/054904, mailed on Aug. 23, 2021, 5 pages.

\* cited by examiner

HEARING PROTECTION DEVICE

CROSS REFERENCE TO RELATED APPLICATIONS

This application is a national stage filing under 35 U.S.C. 371 of PCT/IB2021/054904, filed Jun. 4, 2021, which claims the benefit of U.S. Provisional Application No. 62/705,057, filed Jun. 9, 2020, the disclosure of which is incorporated by reference in its/their entirety herein.

BACKGROUND

Hearing protection devices, including hearing protectors that include muffs worn over the ears of a user, are well known and have a number of applications, including industrial and military applications. Many of these devices are worn in outdoor environments where wind is present. There exists a need to enhance the determination of the nature and location of acoustic signals for wearers of hearing protection devices.

SUMMARY

A hearing protection device is presented. The hearing protection device includes a first and second earmuff connected by a connector. The first and second earmuffs are configured to provide level dependent hearing protection. The first earmuff includes a microphone entry, positioned on an exterior of a housing of the first earmuff, the microphone element being configured to receive an ambient sound. The first earmuff also includes a processor configured to process the ambient sound using a level dependent function. The first earmuff also includes a speaker configured to broadcast the processed ambient sound in an interior of the first earmuff. The first earmuff also includes an asymmetrical windscreen configured to enclose the microphone element. The windscreen is coupled to the housing of the first earmuff.

BRIEF DESCRIPTION OF THE DRAWINGS

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above or on top of those other elements.

As used herein, when an element, component, or layer for example is described as forming a "coincident interface" with, or being "on," "connected to," "coupled with," "stacked on" or "in contact with" another element, component, or layer, it can be directly on, directly connected to, directly coupled with, directly stacked on, in direct contact with, or intervening elements, components or layers may be on, connected, coupled or in contact with the particular element, component, or layer, for example. When an element, component, or layer for example is referred to as being "directly on," "directly connected to," "directly coupled with," or "directly in contact with" another element, there are no intervening elements, components or layers for example.

One common drawback of a hearing protection device is that such a device can diminish the auditory situational awareness which includes the ability of a user to detect, identify/recognize and identify the originating location of sound sources. Localizing the origin of a sound source is a concept understood as spatial situational awareness. The outer ear (i.e. pinna and ear canal) together with the other parts of the ear provide the spatial cues from binaural hearing and enhances the ability for the brain to process these cues and localize sounds. When a headset is worn, the pinna is covered, resulting in distortion of the outer ear function. Such determination of spatial locations of sound sources is important for a user's situational awareness, whether the application is industrial or military.

In outdoor and indoor situations, the spatial situational awareness is provided by the time and level differences between the left and the right ear together with the structure of the outer ear. The directional frequency response, often denoted as the Head-Related Transfer Function (HRTF), can characterize these effects of the outer ear. Reproducing situational awareness in an over-the-ear hearing protection device is particularly difficult, particularly when wind noise is present since wind noise is also reducing the situational awareness even without hearing protection. A good signal to noise ratio is needed between the sound source and the wind noise. One example of a previous solution for providing localization indicia has been discussed, for example in Published United States Patent Application Publication No. 2017/0374455, published on Dec. 28, 2017. However, it is particularly difficult to replace the special cues provide from a human outer ear for ambient sounds received by a microphone and provided to a user through a hearing protection device. Wind noise can also obscure sound source information, both for a human ear as well as for a hearing protection device such as that of US PAP No. 2017/0374455, or other hearing protection devices, such as those that process received sound using a level dependent functionality. Many hearing protectors retrieve the spatial information by the geometry design and position of the microphone entry. Spatial information of incoming sounds can be better generated and preserved by carefully designing a position and orientation of a microphone entry. No additional signal processing is then needed to provide a user with spatial information, similar to how it would be received naturally, by the outer ear without hearing protection.

The windscreen should completely contain the microphone entry to avoid wind approaching the microphone element. However, space is limited for the size of the windscreen, especially in the (with respect to the wearer) forward and rear directions. Size restrictions apply, particularly due to weight, cost, other earmuff components, and user needs regarding movement and other equipment. Additionally, a windscreen design is also important. The windscreen, together with the microphone entry needs to completely enclose the microphone element. Designs in some embodiments illustrated herein include an asymmetrical windscreen design. An asymmetrical windscreen may be designed by considering windscreen dimensions with regard to the airflow patterns around the head and earmuff. The windscreen can extend more in directions where the wind noise exposure is larger/worse to improve wind noise performance. Identifying the directions where the exposure is lower, compared to the worse directions, would enable a smaller windscreen in that direction.

Some embodiments described herein also decrease a microphone entry size by using a directional microphone. A directional microphone would introduce a directional frequency response filtering which then can be excluded from the mic entry geometry. This potentially decreases the volume occupied by the microphone entry.

The composition of the windscreen is also important. The windscreen needs to be resistant to water and tearing. Cloth or fur windscreen options may be available. In some embodiments, a foam windscreen is also preferable. The foam may be a polymeric foam, such as a polyester foam. The foam may be a fine cell reticulated polyester foam in some embodiments. However, other polymeric foams may also be suitable.

Improved wind noise reduction of the ambient sound will not only improve the auditory situational awareness including the localization of sound, but will also improve the vital function of communication to nearby people. The windscreen design is consequently central for both awareness and communication. Windscreen designs and microphone placement are discussed in several different potential embodiments herein.

As noted above, currently used headsets suffer the common draw back of diminished ability of a user to identify the originating location of sound sources, due to the covering of the outer ears and their ability to aid in spatial cues for the brain's processing of sound localization. The main cues for sound localization by the human hearing organ relates either to interaural time difference (ITD), interaural level difference (ILD) and the directional frequency response. For all these cues the preferred microphone design would be a geometry and position identical to the user's ear. For level-dependent-function-enabled hearing protectors, a preferred microphone design for sound localization is a geometry identical to the user's ear. A preferred microphone design for wind noise reduction is a geometry like the "big size" handheld "outdoor TV studio microphone". However, due to size and other design constrains, neither of these implementations are feasible. An intermediate design that satisfies both requirements is needed. This invention solves the optimization between the two needs and combines it with robust design and good LDF feedback characteristics. The present description provides a solution, and a means to enhance spatial situational awareness of users of hearing protection devices.

Microphones described in embodiments herein may include omnidirectional microphone elements (i.e. microphones picking up sound with equal sensitivity from all directions). Other configurations are also envisioned.

Figure 1A:
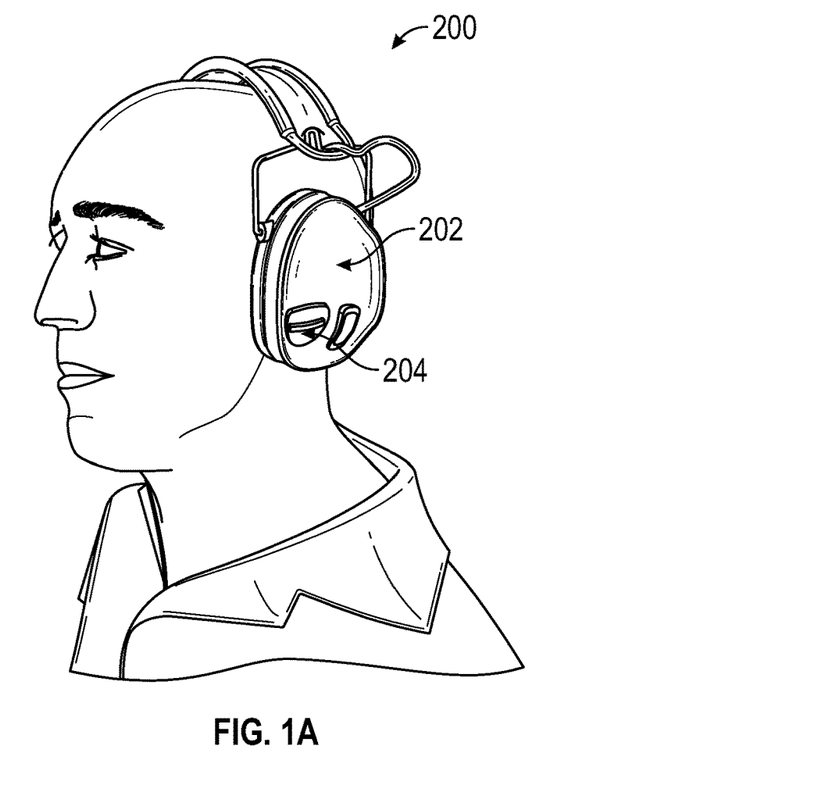
FIGS. 1A-1D illustrate hearing protection devices in accordance with embodiments herein.

FIGS. 1A-1D illustrate hearing protection devices in accordance with embodiments herein. Several different positions may suitably provide the desired features discussed above. FIG. 1A illustrates a hearing protection device 200 with a pair of earmuffs 202. The position of the microphone 204 on earmuff 202 is central for level dependent functionality, but options are limited using common design constraints on the earmuff housing due to weight, cost, and user convenience. The normal position of the microphone 204, as illustrated in FIG. 1A is on the side of the earmuff 202, facing the forward direction. In this position, the size of the windscreen is limited due to robustness. The design opportunities to improve the directional characteristics of the microphone alone are poor due to size of the microphone element and its proximity to the earmuff 202.

Figure 1B:
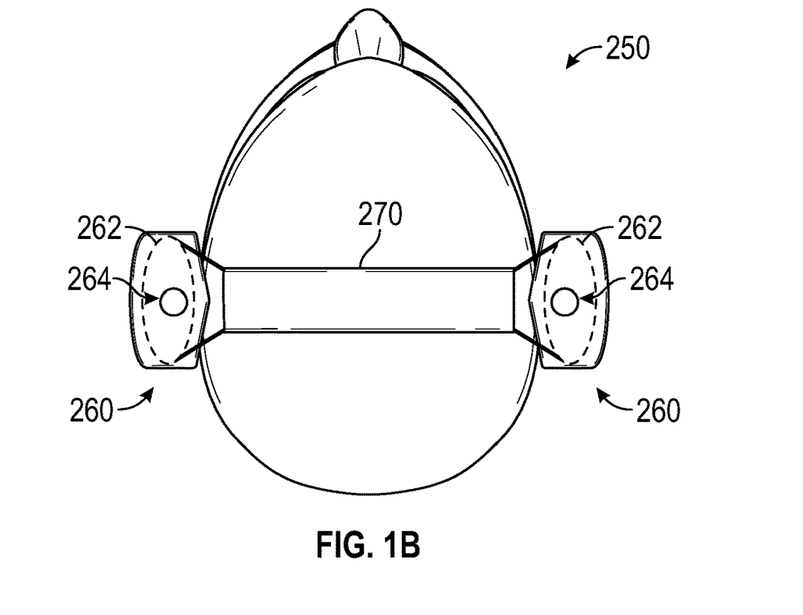

FIG. 1B illustrates an alternative arrangement of a microphone entry 264 within a windscreen 262 on an earmuff 260 of a hearing protection device 250. A hearing protection device 250 includes two earmuffs connected by a headband, or other suitable connector 270. As illustrated in FIG. 1B, when the windscreen 262 is placed on the top of earmuff 260, additional design changes are possible.

When placed on top of the earmuff 260, the size constrains on microphone entry 264 and windscreen 262 are more lenient in both the forward and backward directions, as well as extending outward from a wearer's head. As used herein, a microphone refers to both the microphone element, the wires connecting the element to the PCB board, and the microphone entry. This enables a larger foam windscreen 262 to be used, which improves wind noise reduction. Additionally, traditionally spherical, or symmetrically shaped windscreens are used, but designs illustrated herein allow for asymmetrical designs, e.g. with respect to the front-back direction, to be used as well. This improves wind noise reduction where the largest wind effect is present. Additionally, the position of microphone entry 264 closer to the head of a wearer should also imitate the sound localization cues of inter level differences (ILD) and inter time differences (ITD) better. The windscreen, in some embodiments, is made of a foam with an open, or semi-open, cell structure, which includes a range of about 30% to about 95% of open cells in the cell structure. In some embodiments, the cells are in a size range of 0.2-5 mm. The mic is positioned either under the windscreen if the screen is flat, or within the windscreen if the screen is spherical. The windscreen could be used by any material allowing for an appropriate flow resistivity.

As illustrated in FIGS. 1A and 1B, the windscreen 262 is larger than microphone entry 264. The volume of the microphone entry can be defined as the geometry which has an effect on the acoustic performance of the mic element. However, the windscreen can also have a minor attenuating effect on high frequencies. However, the windscreen is intended to be defined volumetrically separately from the microphone entry for volumetric comparisons. In one embodiment, windscreen 262 has a volume at least twice that of microphone entry 264. In another embodiment, windscreen has a volume at least three times that of microphone entry 264. In another embodiment, windscreen has a volume at least four or five times that of microphone entry 264. The hollow space within the mic entry can also be "filled" with the windscreen which also makes the ratios possible to stretch further.

Figure 1C:
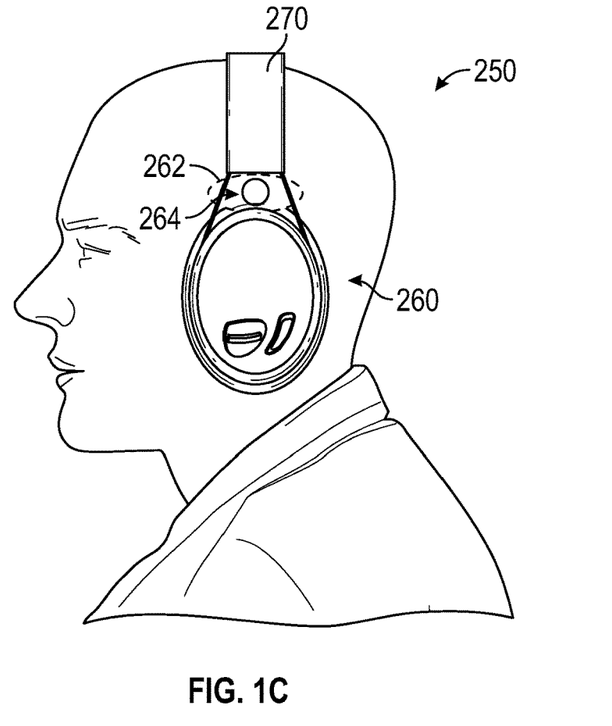

While FIGS. 1B and 1C illustrate a microphone entry 264 positioned on top of an earmuff 260, similar results may be obtained in other positions on the earmuff 260. Microphone entry 264 may also be placed below the earmuff 260, for example, on an opposing side of connector 270. In other embodiments, the mic is positioned on the main cup and the windscreen is included as part of the earmuff housing.

Figure 1D:
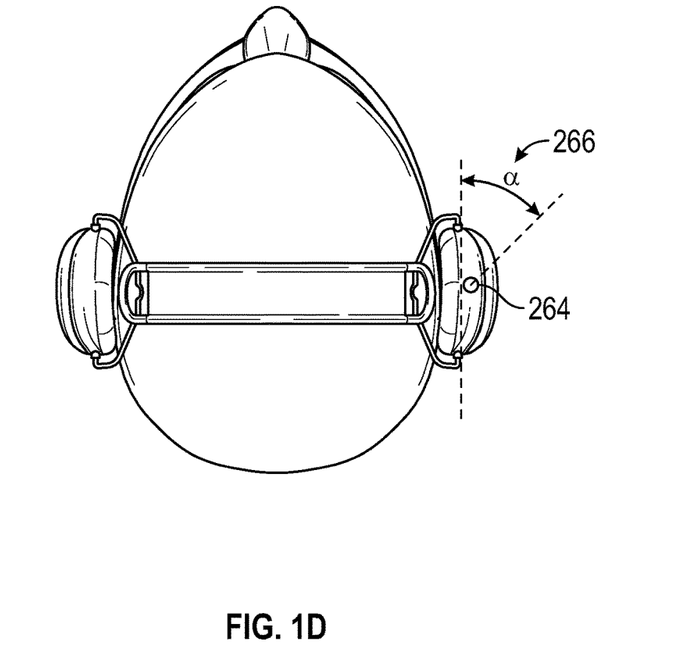

FIG. 1D illustrates a range of angles 266 at which a microphone entry 264 may be oriented with respect to a 'forward' direction in line with a user's head. Microphone entry 264 may be a directional microphone and may be positioned, as discussed in greater detail with regard to FIGS. 2C and 2D, to mimic the structure of the human ear, specifically the directionality of the ear canal and the structure of the pinna. A given microphone entry 264 may need to be positioned at an angle in order to achieve a similar frequency response to the human ear. The angle the microphone may need to be positioned on the headset may differ from microphone to microphone, and may be anywhere from 0-180°.

Figure 2A:
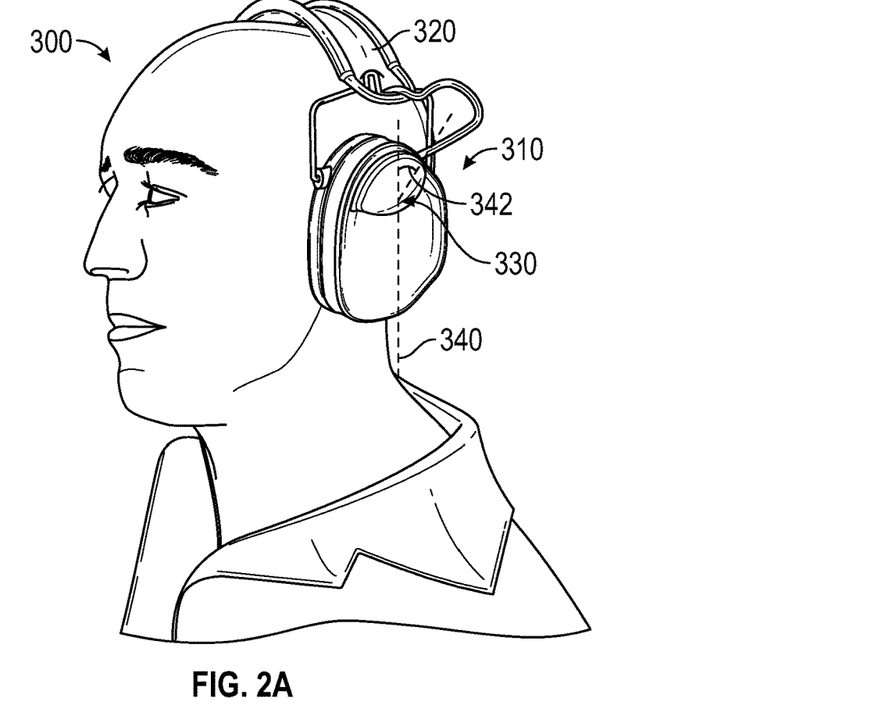
FIGS. 2A-2D illustrate potential placement options of microphones on hearing protection devices in embodiments herein.
Figure 2B:
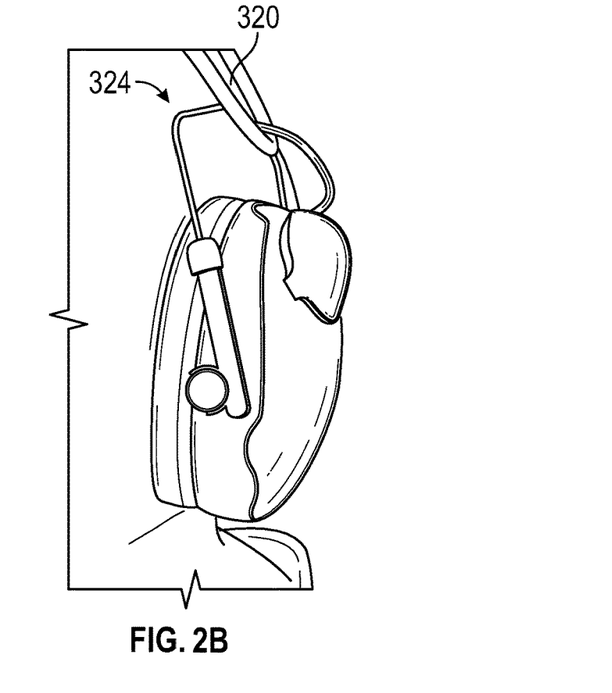

FIGS. 2A-2D illustrate potential placement options of microphones on hearing protection devices. A hearing protection device 300 includes a pair of earmuffs 310 connected by a connector 320. A windscreen shielded microphone 330 is coupled to an exterior of earmuff 310. As illustrated in FIG. 2A, windscreen shielded microphone 330 is positioned substantially in the middle of earmuff 310, as illustrated by axis 340, which is illustrated as bisecting earmuff 310. Windscreen shielded microphone may be positioned in an upper portion of the exterior of the earmuff 310, as illustrated in FIG. 2B. However, as discussed with respect to FIGS. 1A and 1B, a windscreen shielded microphone may also be positioned on top of earmuff 310, for example coupled to an exterior of earmuff 310 between connecting springs 324 and connecting strap 320. Additionally, in some embodiments, windscreen shielded microphone 330 may be directly coupled to connecting springs 324, to connecting strap 320 and not directly coupled to earmuff 310. In the embodiment of FIGS. 2A and 2B, the windscreen is made of a foam material which provides the needed wind noise reduction without deteriorating the frequency response. For example, the foam material may be a polymeric foam, such as polyurethane or polyester foam. The foam may have a cell size between 0.4 and 5.5 mm.

The position of the microphone and windscreen should enable a robust and size generous design together with acceptable feedback characteristics. Feedback is the phenomenon when sound from the loudspeaker element inside the cup reaches the microphone element on the outside. If the gain of this closed loop (including the electronic circuit) is higher than unity an annoying tonal sound will occur. To avoid feedback the transmission path between the speaker and the mic is preferred having as high attenuation as possible. The microphone should have a directionality that makes the frequency response similar to the head related transfer function (HRTF) of the ear. The microphone entry should mimic the directional properties of the HRTF. In one embodiment, an omnidirectional microphone is used. In some embodiments, the microphone is sealed to the exterior of the muff 310, for example using a suitable adhesive or varnish. Other methods of connection including mechanical fasteners are also envisioned.

In one embodiment, a directional microphone is used. The directional microphone has an open backside to the earmuff 330. The microphone is positioned at an angle with respect to the head of a user in the horizontal plane. In one embodiment, the microphone is acutely angled with respect to the connector, as indicated by angle 342. In one embodiment, angle 342 is approximately 45°. However, angle 342 may, in one embodiment, be about 0°, 5°, 10°, 15°, 20°, 25°, 30°, 35°, 40°, 50°, 55°, 60°, 65°, 70°, 75°, 80° or 85° or even about 90°. In some embodiments, a tube is positioned in front of the microphone, opposite the earmuff 330 to add as to mimic the natural resonance of the ear canal. Creating a geometry that mimics the shape of the inner ear is possible but not necessary to attach to the microphone element to further improve the directional frequency response.

In some embodiments, the windscreen is positioned such that a space is present between the microphone surface and the interior of the windscreen. In some embodiments, the windscreen is in a free flow field. In the same way as a handheld microphone, the top position avoids a surface partially surrounding the microphone element.

In some embodiments, the connecting band 320 is designed as to avoid turbulence generation to the microphone and also to facilitate robustness of the microphone entry. In one embodiment, the microphone is attached to the earmuff 310 with electrical wires going directly into the earmuff 310. In another embodiment, the circuit board of microphone 330 can be attached to the headband 320 where the electrical wires are consolidated to the headband cable.

Figure 2C:
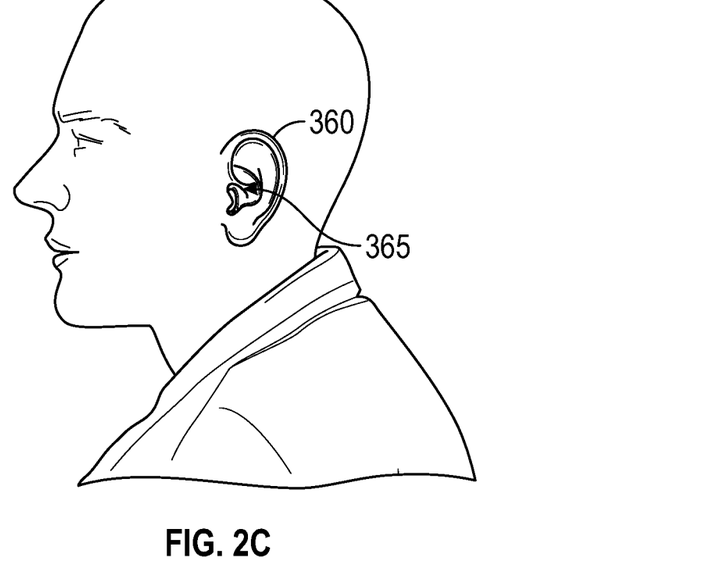

FIG. 2C illustrates a side view of a potential user. The outer portion 360 of the ear, often referred to as the pinna or the auricle, functions as a kind of funnel which assists in directing sound signals further into the ear, toward the ear canal and ear drum, as indicated by arrow 365. The pinna together with the ear canal also performs a spectral transformation on incoming sounds, which enables vertical and horizontal localization by the human brain. The pinna provides filtering in both the vertical and horizontal planes, but can be directionally dependent, for example affecting sounds more that come from above than those from straight ahead.

Figure 2D:
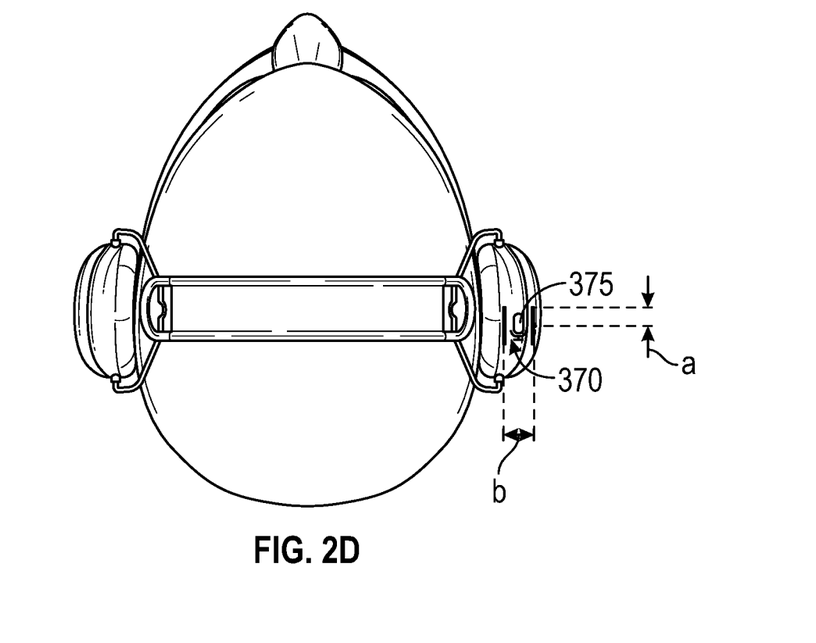

The localization effects provided by the pinna are lost to a user wearing a headset with over-the-ear muffs. FIG. 2D illustrates one embodiment of a microphone assembly that is intended to mimic the function of the outer ear and provide natural localization. For example, a geometry similar to an ear canal may be used, with a reduced geometry of a pinna.

The windscreen is removed for ease of understanding. In one embodiment, as illustrated in FIG. 2D, a hollow structure 370, such as a tube, extends from the microphone outward. In some embodiments, as illustrated in FIG. 2D, the microphone 375 is at least partially enclosed by the hollow structure 370. The hollow structure 370, as illustrated in FIG. 2D, may have both ends open, in some embodiments, or may have an end behind the microphone 375 closed, or partially closed. However, while a tube is illustrated, a cone structure could also be used, narrowing as it approaches the microphone. The hollow structure may be curved, or may be straight, as illustrated in FIG. 2D, or may include an arc shape. The ear canal typically has dimensions, as illustrated in FIG. 2D of about 0.7 cm, as indicated by the "b" reference, and 2.5 cm, as indicated by the "a" reference. The hollow structure 370 is in one embodiment, structured to mimic a human ear canal, as illustrated by the length "a" extending from a microphone membrane, and may have dimensions that vary based on the technical implementation of the pinna and the intended user, for example smaller for child users and larger for adult users.

Figure 3:
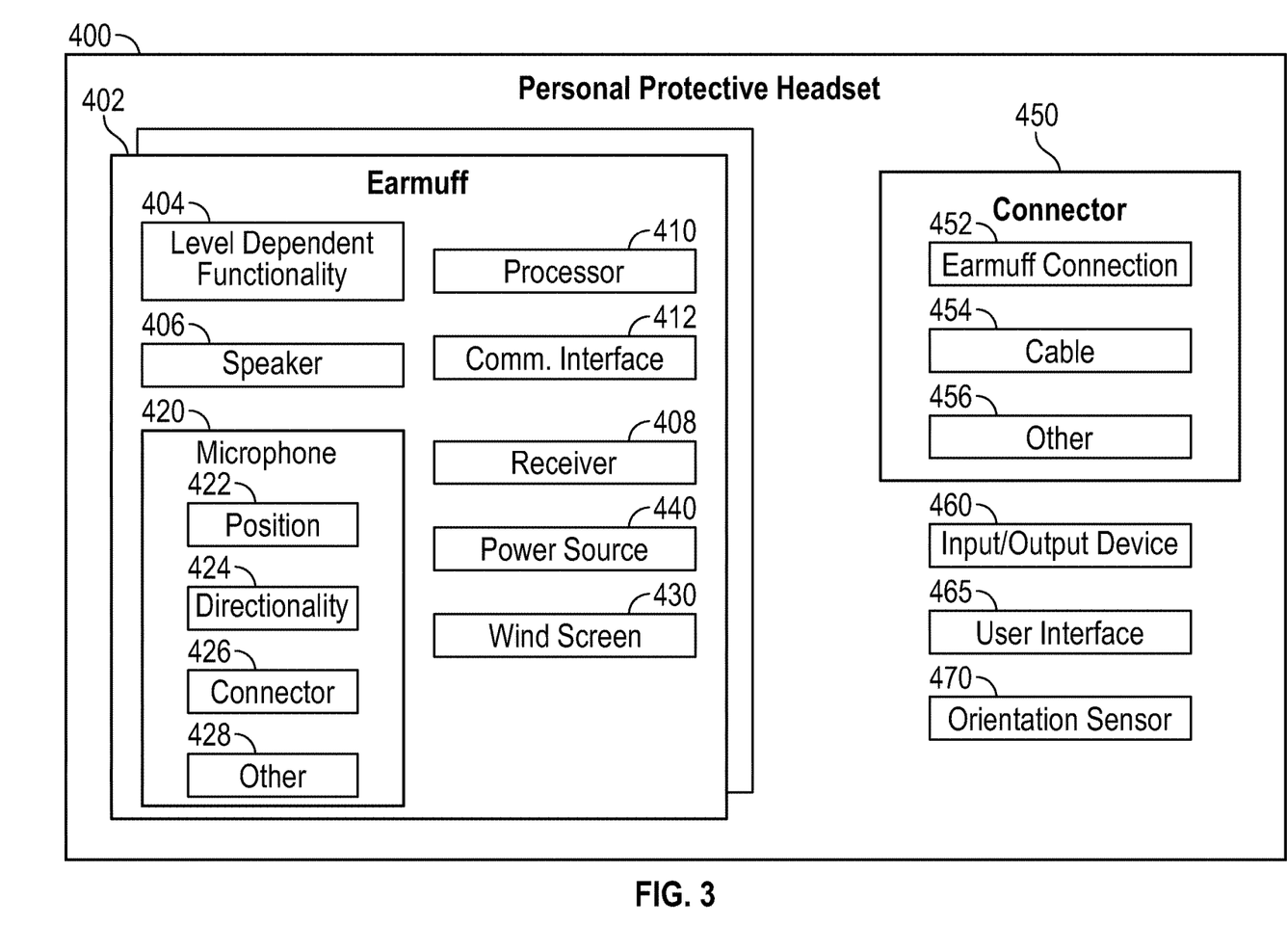
FIG. 3 illustrates a block diagram of a personal protective headset in accordance with embodiments herein.

FIG. 3 illustrates a block diagram of a personal protective headset in accordance with embodiments of the present invention. A personal protective headset 400 includes two earmuffs 402, configured to be worn over the ear of a user, connected by a connector 450. As illustrated in FIGS. 2A and 2B, connector 450 may include a padded strap that connects to each earmuff 402 using an earmuff connection 452. In some embodiments, earmuff connection 452 provides at least some biasing force to help keep earmuffs 402 over a wearer's ear. Connector 450 may also facilitate a cable that connects earmuffs 402 and provides some data communication functionality. Connector 450 may also include other features 456, such as storage for a processor associated with microphone 420.

Earmuff 402 includes an exterior cup and at least some cushion for a user that provides at least some passive hearing protection. Earmuff 402 provides level dependent functionality 404, one version of which is described, for example, in U.S. Provisional Patent Application with Ser. No. 62/947,115, filed Dec. 12, 2019, which is incorporated by reference herein. Additionally, earmuff 402 may provide level dependent functionality 404 in conjunction with another hearing protection device, in a dual protection mode, for example using processor 410 to enter and operate in a dual hearing protection mode, as described in U.S. Provisional Patent Application with Ser. No. 62/909,989, filed on Oct. 3, 2019, which is incorporated by reference herein. Additional level dependent functionality is described in European Patent Application No. 19211305.8, filed on Nov. 25, 2019.

Some active hearing protection units are level dependent, such that an electronic circuit adapts the sound pressure level. Level dependent hearing protection units help to filter out impulse noises, such as gunshots from surrounding noises, and/or continuously adapt all ambient sound received to an appropriate level before it is reproduced to a user. Active hearing protection units, specifically level dependent active hearing protection units, may be necessary to facilitate communication in noisy environments, or environments where noise levels can vary significantly, or where high impulse sounds may cause hearing damage. A user may need to hear nearby ambient sounds, such as machine sounds or speech, while also being protected from harmful noise levels. Active hearing protection can also be used to increase environmental awareness by amplifying soft sounds.

Embodiments described herein provide systems and methods for using a pair of hearing protection devices to reproduce sound at safe levels for a user, with better natural localization indications and reduced wind noise interference. Some embodiments described herein require the first and second hearing protection devices to work in concert to produce a more natural sound than would be produced from two hearing protection devices working independently from each other.

In some embodiments, the level dependent functionality includes a hard limiter, such that, above a certain sound pressure level, sounds are clipped to a particular threshold. Additionally, the amplifier may be disabled when the sound pressure level inside the cup reaches a certain threshold, i.e., the level dependent earpiece amplifier turns off until the sound inside the earmuff falls below the certain threshold.

Earmuff 402 may also provide a wearer with audio received, using receiver 408, from another source. For example, the received audio may be music or other recorded communication provided by a wired or wireless source. Additionally, receiver 408 may also receive communication, such as speech or other sound, from another live source, such as another personal protective headset worn by another individual close or far from the wearer of personal protective headset 400. Earmuff 402 includes a speaker 406 that provides the processed sound to a wearer of the personal protective headset 400. Speaker 406 is located on an inside of the earmuff 402. The components of earmuff 402 are powered by a power source 440, which may be, for example, a rechargeable battery.

Earmuff 402 also includes a microphone 420 located on an exterior of earmuff 402. Microphone 420 has a position on earmuff 402, that may include on an edge of earmuff 402, for example on an edge facing connector 450, or an edge opposite connector 450. Alternatively, while microphone 420 is illustrated in FIG. 3 as part of earmuff 402, microphone 420 may actually be connected to connector 450 or earmuff connection 452. A poor placement of microphone may include a position where it is exposed to force from external objects or where it prevent optimal position of other important objects of the earmuff like buttons, antennas, connectors. Therefore, in some embodiments, microphone 420 may be centered, or substantially centered, on an exterior cup of earmuff 402, under a windscreen 430. Microphone 420 may be on an upper half of the exterior of earmuff 402.

Microphone 420 also includes a directionality 424. In previous designs, a microphone 420 was adhered to a surface of an earmuff such that it was oriented at substantially a 90° angle. However, such positioning does not ideally mimic the outer ear. Therefore, in some embodiments, microphone 420 is directionally angled away from earmuff 402, for example at an acute angle, such that the microphone directionality mimics the frequency response of sound entering the human ear. Depending on a given microphone's geometry, the angle may differ from microphone to microphone.

Microphone 420 provides localization indicia to earmuff 402 through connector 426. In some embodiments, at least some processing by microphone 420 is done on a PCB board associated with connector 450, for example by connector 426 coupling to a cable 454. Alternatively, in some embodiments, microphone 420 communicates through connector 426 to processor 410, which provides necessary computing power for microphone 420. Other features 428 may be associated with microphone 420 as well.

In order to reduce interference from wind noise, microphone 420 is covered by a windscreen 430. In one embodiment, windscreen 430 is made of foam. Windscreen 430 may be shaped such that microphone 420 fits inside a cavity that is sized to receive microphone 420. However, in some embodiments, windscreen 430 includes a cavity that is larger than microphone 420 such that a space is present between microphone 420 and windscreen 430. The space may be, for example, at least about 0.1 mm, 0.2 mm, 0.5 mm, 1 mm, 2 mm, 3 mm, 4 mm, 5 mm, 10 mm or greater.

The processor 410 may include, for example, one or more general-purpose microprocessors, specially designed processors, application specific integrated circuits (ASIC), field programmable gate arrays (FPGA), a collection of discrete logic, and/or any type of processing device capable of executing the techniques described herein. In some embodiments, the processor 410 (or any other processors described herein) may be described as a computing device. In some embodiments, the processor 410 may have or access associated memory configured to store program instructions (e.g., software instructions) that are also executed by the processor 410 to carry out the processes or methods described herein. In other embodiments, the processes or methods described herein may be executed by specifically programmed circuitry of the processor 410. In some embodiments, the processor 410 may thus be configured to execute the techniques for acquiring the origins of a combination of one or more acoustic signals described herein. The processor 410 (or any other processors described herein) may include one or more processors. In some embodiments, some data may be pre-stored in the memory. One or more properties from the sound signals, for example, category, phase, amplitude, and the like may be stored as the material properties data.

The memory may include any volatile or non-volatile storage elements. Examples may include random access memory (RAM) such as synchronous dynamic random-access memory (SDRAM), read-only memory (ROM), non-volatile random-access memory (NVRAM), electrically erasable programmable read-only memory (EEPROM), and FLASH memory. Examples may also include hard-disk, magnetic tape, a magnetic or optical data storage media, and a holographic data storage media.

In some embodiments, the processor 106 may further be configured to classify acoustic signals received. Classifying the acoustic signal or signals may include identifying whether the signal belongs to one or more categories, including but not limited to: background noise, speech, alarms, machine sounds, gunfire, and impulse sounds. Additionally, classifying the acoustic signal or signals may include determining whether the signal is a sound of interest that is previously indicated by the user as the sound of interest sought. As an example, a user may be interested in audible speech signals. The processor 410 may then analyze the acquired sound signals captured by the microphones and indicate (or flag) that the sound aligns with audible speech or that it does not. In this manner, the processor 410 would categorize the sound signal as in agreement or not agreement with the user defined sound of interest.

The hearing protection device 400 of the present description may further include input/output device 460 and user interface 465 to provide visual, audible, haptic, or tactile feedback about sound source location. Where the feedback is audible the means of providing the feedback may be a loudspeaker. Where the feedback is visual, the feedback may be, e.g., blinking lights located in view of a user.

Input/output device 460 may include one or more devices configured to input or output information from or to a user or other device. In some embodiments, the input/output device 460 may present a user interface 465 where a user may define operation and set categories for the sound capture and reproduction device. For example, the user interface 465 may include a display screen for presenting visual information to a user. In some embodiments, the display screen includes a touch sensitive display. In some embodiments, a user interface 465 may include one or more different types of devices for presenting information to a user. The user interface 465 may include, for example, any number of visual (e.g., display devices, lights, etc.), audible (e.g., one or more speakers), and/or tactile (e.g., keyboards, touch screens, or mice) feedback devices. In some embodiments, the input/output devices 460 may represent one or more of a display screen (e.g., a liquid crystal display or light emitting diode display) and/or a printer (e.g., a printing device or component for outputting instructions to a printing device). In some embodiments, the input/output device 460 may be configured to accept or receive program instructions (e.g., software instructions) that are executed by the processor 410 to carry out the embodiments described herein.

The hearing protection device may additionally include an orientation sensor 470. The orientation sensor 470 is capable of providing an output for determining device orientation relative to the environment in which the device is operating. Although it may be mounted on the muff, the orientation sensor 470 may be mounted at any appropriate position on the sound capture and reproduction device that allows it to properly determine device orientation (e.g. on the headband between the muffs). In one embodiment, the orientation sensor 470 may include an accelerometer. In another embodiment, the orientation sensor 470 may include a gyroscope. Alternatively, the orientation sensor 470 may include a compass. In some embodiments, a combination, or all three of these elements may make up the orientation. In some embodiments, the orientation sensor 470 will be capable of providing reference points for localization. Examples of orientation sensors 470 may include the ITG-3200 Triple-Axis Digital-Output Gyroscope from Invensense of San Jose, CA, the ADXL345 Triple-axis Accelerometer from Analog Devices of Norwood, MA, or the HMC5883L Triple Axis Digital Magnetometer from Honeywell of Morrisville, NJ.

Communication interface 412 may be a network interface card, such as an Ethernet card, an optical transceiver, a radio frequency transceiver, or any other type of device that can send and receive information. Other examples of such communication interfaces may include Bluetooth, 3G, 4G, and WiFi radios in mobile computing devices as well as USB. In some examples, personal protective headset 400 utilizes a communication interface 412 to wirelessly communicate with external devices such as a mobile computing device, mobile phone, workstation, server, or other networked computing device. As described herein, communication interface 412 may be configured to receive sounds signal categories, updates, and configuration settings as instructed by processor 410.

Figure 4:
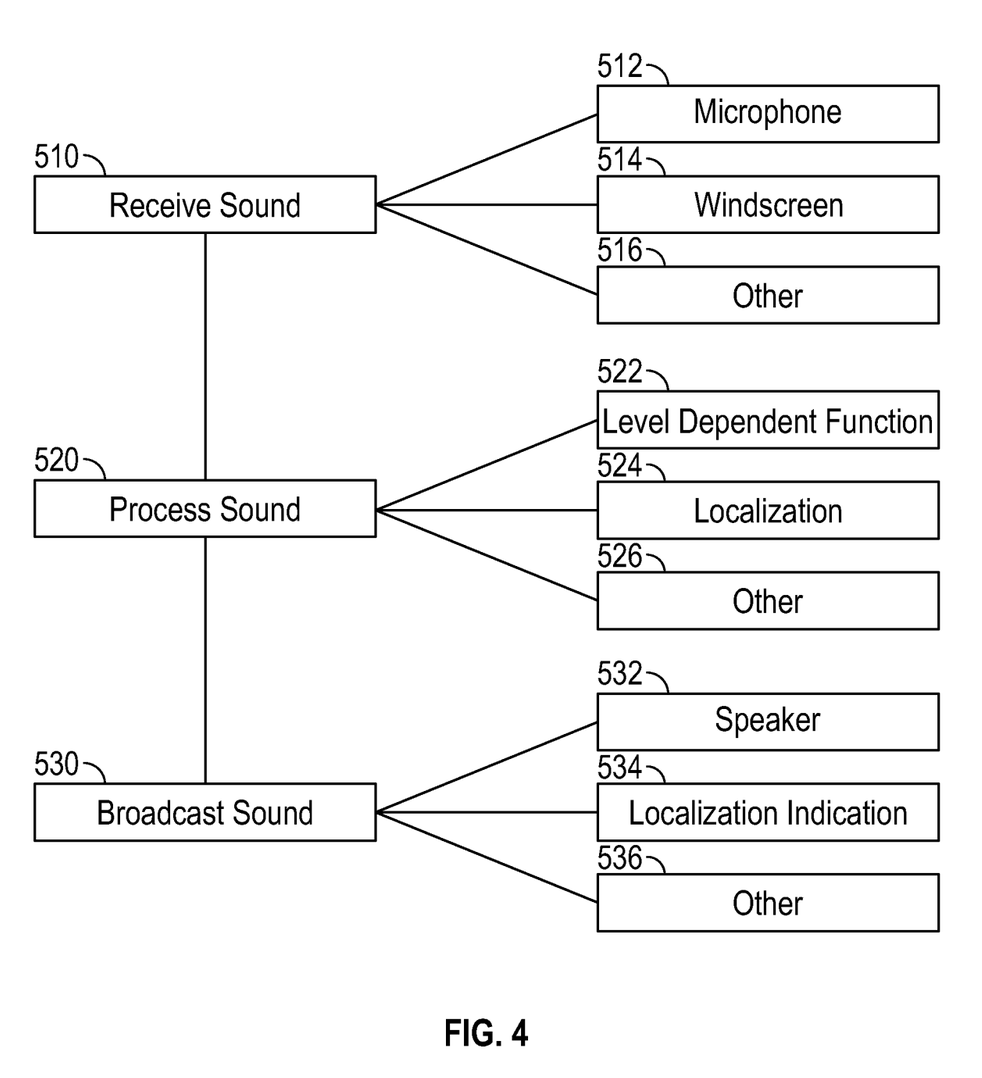
FIG. 4 illustrates a method of processing sound using a hearing protection device in accordance with embodiments herein.

While the hearing protection device 400 includes earmuffs with active hearing protection, each of the protective muffs may also have at least a certain passive noise damping, and a microphone disposed on the exterior, a loudspeaker disposed in the interior, and an amplifier for amplifying acoustic signals received by the microphone and passing the signals onto the loud speaker. FIG. 4 illustrates a method of processing sound using a hearing protection device in accordance with embodiments herein.

In block 510, an ambient sound is picked up by a microphone 512 located on an exterior of a hearing protection device. The microphone 512, in embodiments herein, is sheltered by a windscreen 514. The windscreen 514 may be a foam windscreen that fits over microphone 512. In some embodiments the fit between windscreen 514 and microphone 512 includes a space between the microphone surface and the interior of windscreen 514. Microphone 512 may be directionally positioned at an angle with respect to the exterior of an earmuff cup to mimic a frequency response of a human ear, for example between about 0° 90°. However, other angles may also be suitable. Microphone 512 may have other features 516. The microphone may be a directional microphone, in some embodiments.

The received sound is processed, in block 520, by applying a level dependent function 522. Additional localization processing 524 may be provided. However, in some embodiments no additional localization processing or indications are needed because the positioning of microphone 512 is sufficient to mimic the localization information that would be perceived by the user's outer ear, if it were not covered. In one embodiment, the microphone assembly is shaped to mimic the pinna. Other processing 526 may also be done, in some embodiments.

The sound is broadcast to a user in block 530, using a speaker 532 located on an interior of the earmuff. A localization indication 534 may also be provided, in some embodiments, using an interface associated with a personal protective equipment worn by the user. Broadcasting the sound may also include other features 536, for example interacting with another hearing protection device in a dual mode hearing protection setup.

Figure 5A:
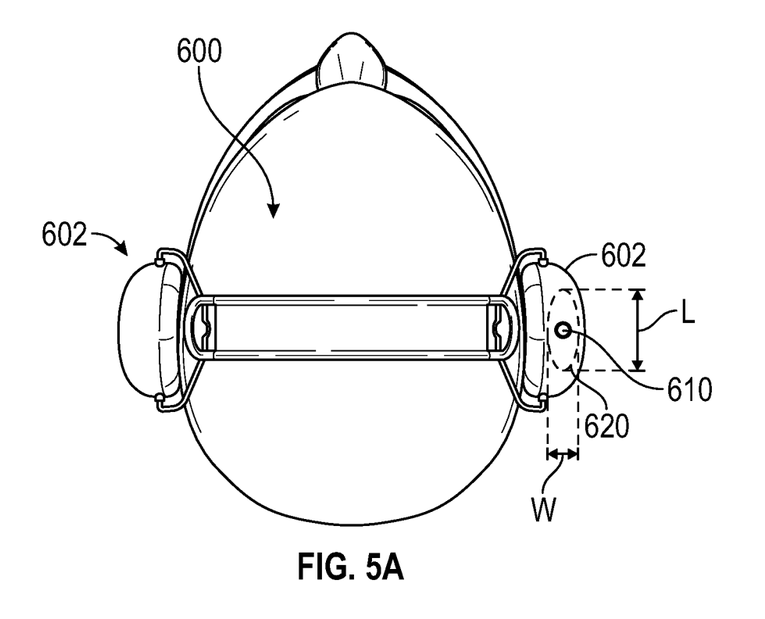
FIGS. 5A-5B illustrate embodiments of personal protective headsets.
Figure 5B:
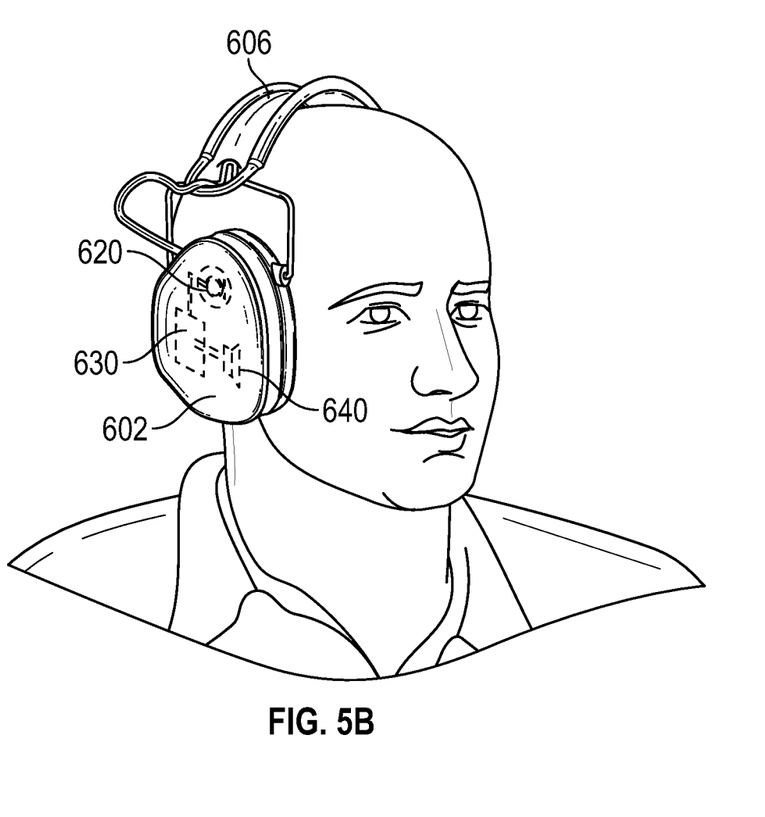

5A-5B illustrate embodiments of personal protective headsets. FIG. 5A illustrates a top-down view of a user wearing a headset 600, which has two earmuffs 602. On one of the earmuffs is a microphone element 610 within a windscreen 620. Windscreen 620 is illustrated as transparent to show the position of microphone 610 only. It is expressly contemplated, as illustrated previously, that windscreen 620 can be made from a foam or other non-translucent material. In one embodiment, as illustrated in FIG. 5A, microphone 610 is positioned in the center of the windscreen, which gives equal priority to filtering wind sounds from e.g. 0 and 180°. However, microphone 610 could be positioned closer to the front of the windscreen, which would give priority to wind sounds closer to 180°. Similarly, positioning microphone 620 further back would give priority to wind sounds closer to 0°. Windscreen can be defined by two dimensions, a length L and a width W. In some embodiments, the relationship between L and W is defined by Equation 1, below:

$$1 < \frac{L}{W} < 20 \qquad \text{Equation 1}$$

Additionally, as described with respect to FIG. 2D, a hollow element (not shown in FIG. 5A), may extend from microphone 612 to windscreen 620, and may extend at least partially through windscreen 620, in some embodiments. Microphone 610 may be directionally oriented on earmuff 602, in some embodiments. In other embodiments, a hollow element provides some directionality as sounds are directed toward microphone 620.

FIG. 5B illustrates a component diagram of a personal protective equipment headset. A headband 606 connects two earmuffs 602 (only one shown in FIG. 5B), over the head of a user. On at least one of the earmuffs 602 is a microphone entry 612, which includes a microphone element (not shown in FIG. 5B). Microphone entry 612 is completely enclosed by a windscreen 620, which is completely sealed to earmuff cup 602, in one embodiment, so that air or wind cannot slip in between the windscreen 620 and housing 602. Illustrated in FIG. 5B are several components that are inside the earmuff housing 602 including, but not limited to, an electric circuit board 630, which processes sound received by microphone 610, for example using a level dependent function. Processed sound is provided to an internal speaker 640, which broadcasts the sound into a user's ear at a safe level.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

A hearing protection device is presented. The hearing protection device includes a first and second earmuff connected by a connector. The first and second earmuffs are configured to provide level dependent hearing protection. The first earmuff includes a microphone entry, positioned on an exterior of a housing of the first earmuff, the microphone element being configured to receive an ambient sound. The first earmuff also includes a processor configured to process the ambient sound using a level dependent function. The first earmuff also includes a speaker configured to broadcast the processed ambient sound in an interior of the first earmuff. The first earmuff also includes an asymmetrical windscreen configured to enclose the microphone element. The windscreen is coupled to the housing of the first earmuff.

The hearing protection device may be implemented such that the asymmetrical windscreen includes a longest vertical dimension and a longest horizontal dimension. The longest horizontal dimension is greater than the longest vertical dimension.

The hearing protection device may be implemented such that the asymmetrical windscreen is ovular in shape.

The hearing protection device may be implemented such that the longest horizontal dimension is two times greater than the longest vertical dimension.

The hearing protection device may be implemented such that the longest horizontal dimension is five times greater than the longest vertical dimension.

The hearing protection device may be implemented such that the microphone element is positioned off-center from the asymmetrical windscreen.

The hearing protection device may be implemented such that the fully enclosing the microphone element includes the windscreen sealed to the housing.

The hearing protection device may be implemented such that a surface area of the asymmetrical windscreen is five times greater than a surface area of a membrane of the microphone element.

The hearing protection device may be implemented such that the microphone is a directional microphone with an entry position that is angled with respect to the exterior of the housing.

The hearing protection device may be implemented such that the directional microphone is positioned such that is substantially centered with respect to the housing of the first earmuff.

The hearing protection device may be implemented such that the directional microphone is positioned on an upper portion of the housing of the first earmuff, such that it is closer to the connector than to a point on the housing furthest from the connector.

The hearing protection may be implemented such that the microphone element is substantially centered within the windscreen.

The hearing protection device may be implemented such that it also includes a hollow portion extending from the microphone element.

The hearing protection device may be implemented such that the hollow portion is curved from the directional microphone and directs sound into the microphone.

The hearing protection device may be implemented such that the hollow portion includes a tube.

The hearing protection device may be implemented such that the hollow portion includes a cone.

The hearing protection device may be implemented such that the hollow is sized such that a space is present between an interior side of the windscreen and a surface of the microphone.

The hearing protection device may be implemented such that the microphone is coupled to an earmuff connection feature of the connector.

The hearing protection device may be implemented such that the windscreen includes a polymeric foam.

The hearing protection device may be implemented such that the microphone is coupled to the processor. The processor is located within the earmuff.

The hearing protection device may be implemented such that the second earmuff includes a second microphone, positioned on an exterior of a second housing of the second earmuff, the second microphone being configured to receive a second ambient sound. The second earmuff may also include a second processor configured to process the second ambient sound using a second level dependent function. The second earmuff may also include a second speaker configured to broadcast the second processed ambient sound in an interior of the second earmuff. The second earmuff may also include a second windscreen with a second hollow that fully encloses the second microphone. The second windscreen may be a foam.

The hearing protection device may be implemented such that the first level dependent function and the second level dependent function are similar.

The hearing protection device may be implemented such that it also includes a rechargeable battery that is configured to provide power to the microphone, processor and speaker.

The hearing protection device may be implemented such that the windscreen provides substantially equal wind noise reduction from all angles.

The hearing protection device may be implemented such that the windscreen is substantially centered along a width of the earmuff.

The hearing protection device may be implemented such that the windscreen is positioned closer to a connector side of the earmuff than an opposing side of the earmuff.

The hearing protection device may be implemented such that the windscreen fully encloses the microphone element.

The hearing protection device may be implemented such that the windscreen, in combination with the housing, fully encloses the microphone element.

A method of providing hearing protection using a hearing protection device is presented. The method includes receiving an ambient sound, through a microphone on an exterior of an earmuff of the hearing protection device. The microphone is fully enclosed by a windscreen sealed to the exterior of the earmuff such that the microphone is fully enclosed by the windscreen. The windscreen has a height and a width, and the width is greater than the height. The method also includes processing the received ambient sound, using a processor of the hearing protection device to apply a level dependent function to convert the received ambient sound to a safe sound. The method also includes broadcasting the safe sound, through a speaker inside the earmuff.

The method may be implemented such that the windscreen is a foam windscreen.

The method may be implemented such that the windscreen substantially centered on the exterior of the earmuff with respect to a width axis parallel to a ground level.

The method may be implemented such that the windscreen is closer to a headband connector side than a side opposite the headband connector side.

The method may be implemented such that the microphone is centered with respect to the windscreen.

The method may be implemented such that the microphone is closer to a front edge of the earmuff exterior than a back edge of the earmuff exterior.

The method may be implemented such that the microphone is closer to a back edge of the earmuff exterior than a front edge of the earmuff exterior.

The method may be implemented such that the microphone is a directional microphone.

The method may be implemented such that the directional microphone is angled with respect to the exterior.

The method may be implemented such that the directional microphone is angled such that sound is received by the microphone entry at a 45° angle.

The method may be implemented such that the directional microphone is positioned along an axis extending substantially parallel to a connector that connects the earmuff to a second earmuff. The connector is configured to be worn over the head of a user.

The method may be implemented such that the earmuff has a connector edge and an opposing edge. The connector edge includes the closest point between the earmuff and a connector that connects the earmuff to a second earmuff. The opposing edge includes an edge furthest from the connector edge on the exterior. The directional microphone is closer to the connector edge than the opposing edge.

The method may be implemented such that the directional microphone is on the connector edge.

The method may be implemented such that the earmuff has a connector edge and an opposing edge. The connector edge includes the closest point between the earmuff and a connector that connects the earmuff to a second earmuff. The opposing edge includes an edge furthest from the connector edge on the exterior. The directional microphone is on the opposing edge.

The method may be implemented such that a tube extends from the microphone toward the windscreen.

The method may be implemented such that the directional microphone is part of a microphone assembly shaped to resemble an ear canal structure.

The method may be implemented such that it also includes receiving a second ambient sound through a second directional microphone on a second exterior of a second earmuff of the hearing protection device. The second microphone is fully enclosed by a second windscreen. The method may also include processing the second received ambient sound, using a second processor of the hearing protection device to apply a second level dependent function to convert the second received ambient sound to a second safe sound.

The method may also include processing the first and second received ambient sounds to obtain a localization indication.

The method may be implemented such that the localization indication is based on a detected difference in the first and second level dependent processing.

EXAMPLES

Figure 6A:
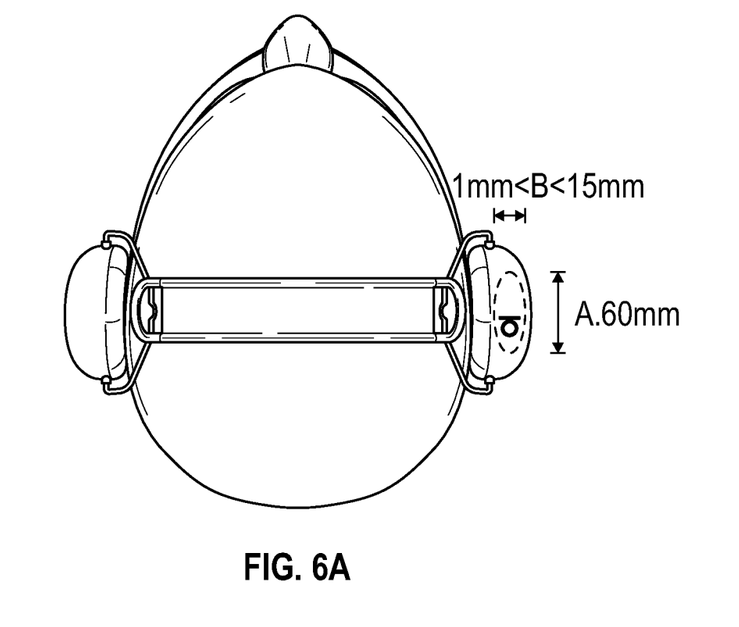
FIGS. 6A-6C illustrate an example set up and results for placement of a windscreen protected microphone on a hearing protection device.
Figure 6B:
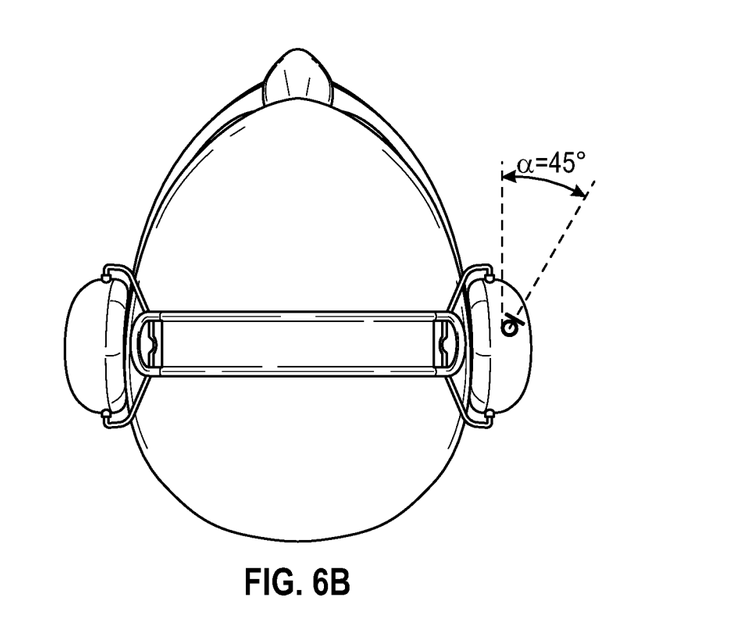

FIGS. 6A and 6B illustrate an example set up and results for placement of a windscreen protected microphone on a hearing protection device.

Example 1

A windscreen consisting of a flat foam of 4 mm thickness with a length A=60 mm and a maximum width of 15 mm which decreases down to 1 mm at both the front and back of windscreen. The microphone element is positioned with ⅔ of cavity in front of the microphone element and ⅓ behind, as illustrated in the schematic of FIG. 6A. A traditional windscreen would have different wind noise reduction dependent on wind direction. The example results in a low and equal wind noise level for all directions.

Example 2

The angle of a directional microphone can be 45 degrees which, depending of the polar pattern of the microphone model, can better mimic the HRTF when comparing 0 degrees frequency response to 45 degrees.

Figure 6C:
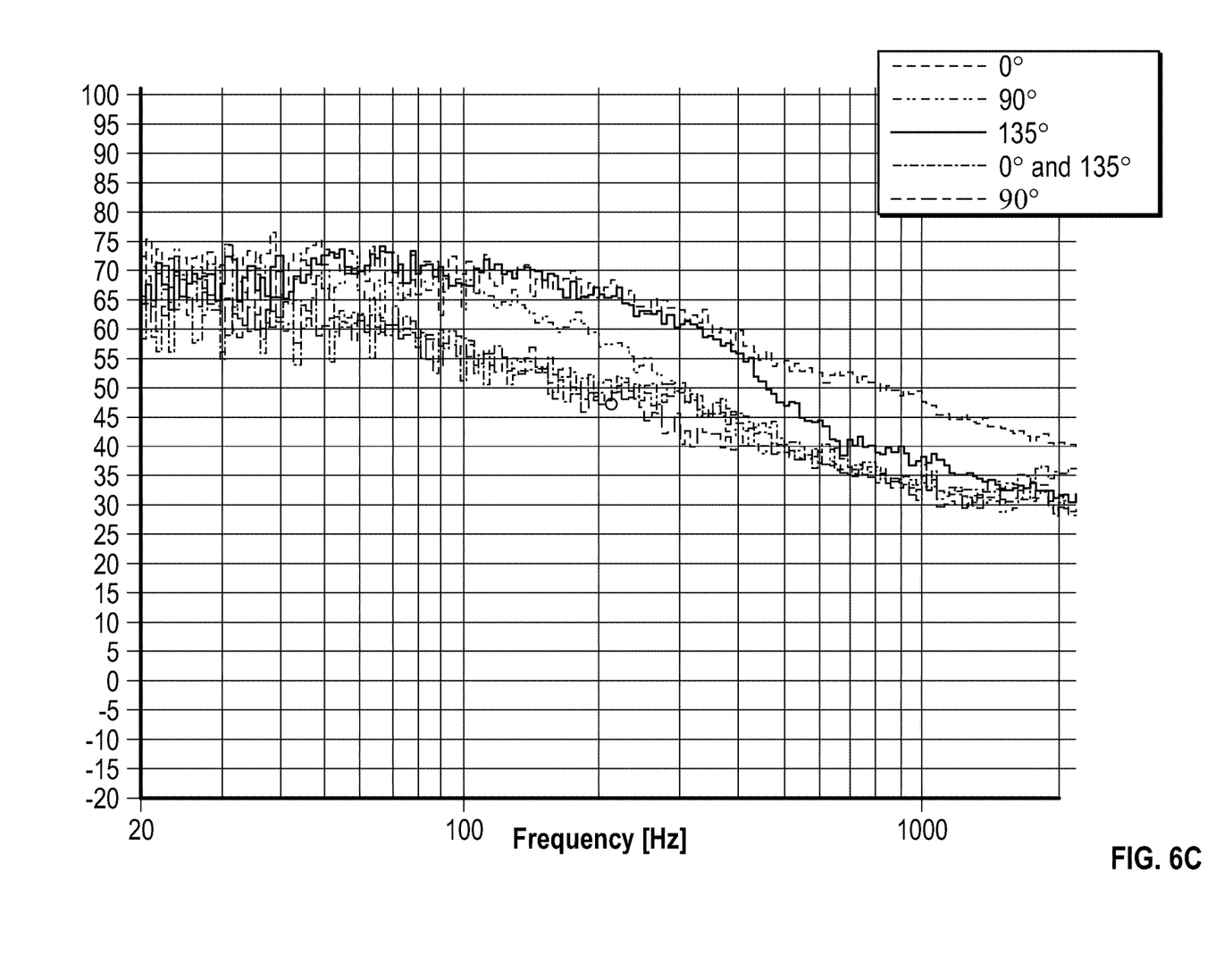

FIG. 6C illustrates recorded wind noises according to IEC 60268-4:2004 for a SportTac™ headset, obtained from 3M Company, at 0°, 90°, 135° compared to the device of Example 1 at 0°, 90° and 135° at 10 m/s.

I claim:

1. A hearing protection device comprising:
   a first and second earmuff connected by a connector, wherein the first and second earmuffs are configured to provide level dependent hearing protection; and
   wherein the first earmuff comprises:
      a microphone;
      a microphone entry, positioned on an exterior of a housing of the first earmuff, the microphone entry being configured to receive an ambient sound;
      a processor configured to process the ambient sound using a level dependent function;
      a speaker configured to broadcast the processed ambient sound in an interior of the first earmuff; and
      an asymmetrical windscreen configured to enclose the microphone entry, and wherein the windscreen is coupled to the housing of the first earmuff, such that the windscreen encloses the microphone entry, wherein the asymmetrical windscreen comprises a longest vertical dimension and a longest horizontal dimension, and wherein the longest horizontal dimension is greater than the longest vertical dimension.

2. The hearing protection device of claim 1, wherein the longest horizontal dimension is two times greater than the longest vertical dimension.

3. The hearing protection device of claim 1, wherein the asymmetrical windscreen has a center, and wherein the microphone entry is positioned off-center from the asymmetrical windscreen.

4. The hearing protection device of claim 1, wherein fully enclosing the microphone element comprises the windscreen sealed to the housing.

5. The hearing protection device of claim 1, wherein the microphone is a directional microphone with the microphone entry being positioned at an angle with respect to the exterior of the housing.

6. The hearing protection device of claim 1, and further comprising a hollow portion extending from the microphone outward.

7. The hearing protection device of claim 6, wherein the hollow portion is curved from the directional microphone and directs sound into the microphone.

8. The hearing protection device of claim 1, wherein the hollow portion is sized such that a space is present between an interior side of the windscreen and a surface of the microphone.

9. The hearing protection device of claim 1, wherein the second earmuff comprises:
   a second microphone, positioned on an exterior of a second housing of the second earmuff, the second microphone being configured to receive a second ambient sound;
   a second processor configured to process the second ambient sound using a second level dependent function;
   a second speaker configured to broadcast the second processed ambient sound in an interior of the second earmuff; and
   a second windscreen with a second hollow portion that fully encloses the second microphone, wherein the second windscreen comprises a foam.

10. The hearing protection device of claim 1, wherein the windscreen provides substantially equal wind noise reduction from all angles.

11. The hearing protection device of claim 1, wherein the windscreen is substantially centered along a width of the first earmuff and wherein the windscreen is positioned closer to a connector side of the first earmuff than an opposing side of the first earmuff.

12. The hearing protection device of claim 1, wherein the windscreen fully encloses the microphone.

13. The hearing protection device of claim 1, wherein the windscreen, in combination with the housing, fully encloses the microphone element.

14. A method of providing hearing protection using a hearing protection device, the method comprising:
   receiving an ambient sound, through a microphone on an exterior of a housing of an earmuff of the hearing protection device, wherein the microphone is fully enclosed by a windscreen sealed to the exterior of the housing of the earmuff such that the microphone is fully enclosed by the windscreen, the windscreen comprising a longest vertical dimension and a longest horizontal dimension and wherein the longest horizontal direction is greater than the longest vertical dimension;
   processing the received ambient sound, using a processor of the hearing protection device to apply a level dependent function to convert the received ambient sound to a processed sound; and
   broadcasting the processed sound, through a speaker inside the earmuff, and wherein the windscreen is a foam windscreen.

15. The method of claim 14, wherein the windscreen is substantially centered on the exterior of the housing of the earmuff with respect to a width axis parallel to a ground level.

16. The method of claim 1 any claim 1, wherein a tube extends from the microphone toward the windscreen.

17. The method of claim 16, wherein the microphone is a directional microphone that is part of a microphone assembly shaped to resemble an ear canal structure.

\* \* \* \* \*

UNITED STATES PATENT AND TRADEMARK OFFICE
CERTIFICATE OF CORRECTION

PATENT NO.         : 12,115,039 B2
APPLICATION NO.    : 18/001126
DATED              : October 15, 2024
INVENTOR(S)        : Oscar Kårekull Page 1 of 1

It is certified that error appears in the above-identified patent and that said Letters Patent is hereby corrected as shown below:

In the Claims

Column 16
Line 66, In Claim 16, delete "The method of claim 1 any claim 1" and insert -- The method of claim 1 --, therefor.

Signed and Sealed this
Seventeenth Day of June, 2025

Coke Morgan Stewart
*Acting Director of the United States Patent and Trademark Office*